United States Patent
Chatelier et al.

(10) Patent No.: US 6,623,747 B1
(45) Date of Patent: Sep. 23, 2003

(54) MULTILAYER MATERIALS

(75) Inventors: Ronald Christopher Chatelier, Bayswater (AU); Liming Dai, Clayton (AU); Hans Jörg Griesser, The Patch (AU); Sheng Li, Highett (AU); Paul Zientek, Glen Iris (AU); Dieter Lohmann, Münchenstein (CH); Peter Chabrecek, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 08/601,420

(22) Filed: Feb. 14, 1996

Related U.S. Application Data

(63) Continuation of application No. 08/240,738, filed as application No. PCT/EP93/02420 on Sep. 8, 1993, now abandoned.

(30) Foreign Application Priority Data

Sep. 14, 1992 (AU) .............................. 4710/92

(51) Int. Cl.[7] .............................. A61F 2/00; C08F 8/00; C08F 8/32
(52) U.S. Cl. ................ 424/422; 424/423; 424/427
(58) Field of Search .................... 424/400, 422–426, 424/427

(56) References Cited

U.S. PATENT DOCUMENTS

| | | | | |
|---|---|---|---|---|
| 4,373,009 A | * | 2/1983 | Winn | 428/424.2 |
| 4,663,233 A | | 5/1987 | Beavers | 428/412 |
| 4,716,154 A | * | 12/1987 | Malson | 514/54 |
| 4,734,475 A | * | 3/1988 | Goldenberg | 526/273 |
| 4,810,638 A | * | 3/1989 | Albarella | 435/7 |
| 4,929,685 A | * | 5/1990 | Kobashi | |
| 5,037,677 A | | 8/1991 | Halpern | 427/338 |
| 5,080,924 A | * | 1/1992 | Kamel | 427/2 |
| 5,258,041 A | * | 11/1993 | Guire | 623/66 |

FOREIGN PATENT DOCUMENTS

| | | | |
|---|---|---|---|
| EP | 276631 | 8/1988 | C08J/7/12 |
| FR | 2649404 | 1/1991 | C08J/7/04 |
| JP | 63309914 | 12/1988 | |
| NZ | 260260 | 4/1994 | |
| WO | 83/03977 | 11/1983 | A61M/25/00 |
| WO | 90/04609 | 5/1990 | C08F/8/00 |
| WO | 93/03776 | 6/1993 | A61L/27/00 |
| WO | WO94/06485 | 3/1994 | A61L/27/00 |

* cited by examiner

Primary Examiner—Gollamudi S. Kishore
(74) Attorney, Agent, or Firm—Jian S. Zhou; Richard I. Gearhart; R. Scott Meece

(57) ABSTRACT

The invention is directed to a composite material, especially a biomedical device, e.g. an ophthalmic device, preferably a contact lens, with one or more wettable surfaces capable of holding a continous layer of aqueous fluid thereon which composite material comprises a bulk material and a hydrophilic coating characterized in that the hydrophilic coating consists of a carbohydrate attached covalently to reactive groups at the surface of the bulk material, either directly or via functional groups of an oligofunctional compound, said oligofunctional compound in turn having functional groups being capable of reacting with said reactive groups at the surface of the bulk material and with the carbohydrate, wherein said reactive groups are either inherently (a priori) present in the bulk material or wherein said reactive groups have been attached to the surface of the bulk material by a plasma surface preparation, as well as to a process of manufacture of such a composite material.

22 Claims, No Drawings

MULTILAYER MATERIALS

This application is a continuation of application Ser. No. 08/240,738 filed on May 12, 1994 now abandoned which is a 371 of PCT/EP93/02420, filed Sep. 8, 1993.

This invention relates to composite materials for biomedical use that possess considerably improved retention of an aqueous layer on the surfaces. The invention also relates to the production of such materials from materials that possess suitable bulk properties, but inadequate retention of an aqueous layer. In a particular aspect, the materials and method of this invention are useful for the fabrication of ophthalmic devices, e.g. contact lenses.

BACKGROUND TO INVENTION

There are many applications of materials where retention of a thin film of aqueous fluid is desirable. For example, the retention of an aqueous fluid layer is beneficial for lubrication of catheters, the retention of an aqueous fluid layer can reduce protein fouling on the surface of pacemakers and artificial vascular grafts, or the retention of an aqueous fluid layer can prevent the colonization of a surface by bacteria as they are unable to attach properly. In another aspect, the facile movement of an eyelid over a contact lens is important for the comfort of the wearer; this sliding motion is facilitated by the presence of a continuous layer of tear fluid on the contact lens, a layer which lubricates the tissue/lens interface. However, clinical tests have shown that currently available contact lenses partially dry out between blinks, thus increasing friction between the eyelid and the lens. The increased friction results in soreness of the eyes and movement of the contact lens. Since the average period between blinks is ca. 12 seconds, it would be advantageous to fabricate a wettable and biocompatible contact lens that can hold a continuous layer of tear fluid for more than 12 seconds. Current biomedical materials do not reach this target; for instance, contact lenses fabricated from highly water swellable polymer pHEMA retain such a tear layer for approximately 5 seconds only.

Thus materials with wettable and biocompatible surfaces are highly desirable for many applications. The wettability of materials is strongly dependent on the chemical composition of the material surface. In particular, the ability of the surface to hold a continuous layer of an aqueous solution, such as tear fluid, is affected by the composition of the material surface. Early attempts to solve the wettability problem in the ophthalmic field were based on producing hydrophilic materials. For example, in an attempt to make wettable soft contact lenses, silicone elastomers with pendant epoxy groups were prepared by crosslinking epoxidized silicone compounds (French patent FR 2,622,201, J. M. Frances and G. Wajs). The elastomers were rendered wettable by grafting glucuronic acid onto the epoxy groups. The disadvantage of incorporating hydrophilic species into polymers by bulk synthesis is that the optimum balance of optical properties (e.g., transparency and refractive index), mechanical properties (e.g. strength, hardness, gas permeability and elasticity) and processability of the material obtainable will be worse than conventional materials and may not satisfy the application. The incorporation of hydrophilic monomers is not appropriate for improving the wettability of fluoropolymer- or acrylate-based lenses.

In an attempt to fabricate hard contact lenses which are compatible with the cornea and ocular fluid, dextran ester monovinyl compounds have been copolymerised with various acrylates (Japanese patent JP 63/309914, H. Kitaguni et al.). Dextran/methyl methacrylate copolymers have been prepared by graft polymerisation and have yielded wettable contact lenses (Y. Onishi et al. in Contemp. Top. Polym. Sci. 4, 149 (1984)). The preparation of dextran ester copolymers by bulk polymerisation methods offers limited scope for improving the wettability of contact lenses in general. The disadvantage of incorporating hydrophilic compounds into polymers by bulk synthesis is that the optical properties (e.g., transparency and refractive index), mechanical properties (e.g., strength, hardness, gas permeability and elasticity) and processability of the material cannot be optimized independently.

A method of modifying the surface of contact lenses has been disclosed in GB 2,163,436 Halpern). According to said method the lens is coated with a carbohydrate which is then crosslinked either covalently with a polyisocyanate or electrostatically with a divalent cation. The process results in a crosslinked skin which is not covalently bonded to the lens and will delaminate when subjected to a shearing force e.g. by an eyelid.

An alternative approach has been disclosed in WO 90/04609 (Sepracor). Polymeric substrates, especially polymeric membranes, having reactive groups such as hydroxy or amino groups at the ends of the polymer chains thereof are reacted with a polyfunctional linker moiety having terminal groups such as epoxy, carbonyl, carboxy, amino, halo, hydroxy, sulfonylhalide, acyl halide, isocyanato, or combinations thereof, which in turn are bonded with a ligand such as hydroxyethylcellulose or dextran. Since the molecular weight of the polymer chains in the substrate is high, the density of chain ends, especially at the surface, will be low, and therefore the density of grafted polysaccharide chains will be low.

The use of dextran and other carbohydrates for surface modification of polymers has also been reported by WO 83/03977, however, in that case the linker moiety is a silane and articles to be treated such as contact lenses are not disclosed.

Additional prior art is directed to modification of the surfaces of contact lenses (U.S. Pat. No. 5,080,924) or ocular implants (WO 93/03776), respectively, wherein amino groups at the surface thereof are reacted with dialdehydes and are then coupled with polysaccharides. However, the reaction of an aldehyde with the hydroxyl groups of a polysaccharide will yield an acid-labile ketal bond.

The above methods all require the presence of the article of a chemically reactive group suitable for the intended covalent reaction. Many materials of interest for ophthalmic applications and implantable biomaterial devices do not possess suitable reactive surface groups, for instance, silicon-based contact lenses and polytetrafluoroethylene vascular grafts. The present invention also comprises methods for the activation of a device surface, the method being generic, so that the surface of any material with suitable bulk properties can be converted to be receptive for the covalent immobilization of a coating which is highly retentious for aqueous layers. In this embodiment of the invention the surface of the polmyeric material is activated preferably by a gas plasma (glow discharge) surface treatment method.

A number of surface treatment techniques for polymeric materials are known in the art: Corona Discharge, Flame Treatment, Acid Etching, and a number of other methods intended to perform chemical modification of the surface. Among the disadvantages of these techniques are the use of or production of hazardous chemicals, the often excessive depth of treatment, non-uniformity of treatment at a microscopic level, and often severe etching and pitting that leads to changes in surface topography. The depth of treatment is important because with clear materials such as those required for lenses the optical clarity and surface smoothness become affected after an excessively harsh treatment.

Treatment of polymeric surfaces by gas plasmas provides the advantages of very low treatment depth, and uniformity on a microscopic scale. A gas plasma (also known as glow discharge) is produced by electrical discharge in a gas atmosphere at reduced pressure ("vacuum"). It creates a stable, partially ionized gas that may be utilized for effecting reactions on the surface of the substrate because the gas plasma environment activates even chemical compounds that are unreactive under normal conditions. The treatment intensity at the surface is generally relatively strong, and yet the penetration depth of gas plasma treatment is very low, of the order of 5 to 50 nanometres, at a treatment intensity sufficient for useful surface modification. Surface topography and optical clarity do not change unless exposure to the plasma is performed for periods of time much exceeding the time required for achieving the desired chemical modification of the surface. There occurs, therefore, significantly less alteration of the properties of the bulk material than with alternative treatment technologies.

Gas plasma techniques can have two classes of outcomes. In the first, commonly called plasma surface treatment, the surface of a polymeric material to be treated ("the substrate") is subjected to a plasma established in one or more inorganic vapors or some select organic vapors, and the plasma treatment causes the replacement of some of the original chemical groups on a polymer surface by other, novel groups which are contributed from the plasma gas. For instance, the plasma surface treatment of polytetrafluoroethylene in an ammonia plasma leads to the abstraction of some of the surface fluorine atoms by C—F bond breakage and the incorporation into the modified surface layer of amine groups by C—N bond formation. Plasma surface treatment in an appropriate vapor such as ammonia, carbon dioxide, or water vapor, can therefore be used to place on the surface of any polymeric material reactive chemical groups, such as amine, carboxyl, or hydroxyl, suitable for the subsequent covalent immobilization of various molecules.

The second type of plasma technique is commonly called plasma polymerization and occurs when a discharge is struck in most organic vapors. In contrast to plasma surface treatment, in which less than a monolayer of new material is added, the technique of plasma polymerization leads to the formation of film coatings which can be several micrometers thick and can completely mask the substrate.

Plasma polymers are also covalently bonded to the underlying substrate. The covalent attachment of the plasma coating to the bulk material ensures that the plasma polymer does not detach. Furthermore, plasma polymers are highly crosslinked and do not possess low molecular weight fragments which might migrate into body tissue or fluids.

By appropriate choice of the monomer vapor and the plasma conditions, plasma polymer coatings can be fabricated to contain specific, chemically reactive groups which are also suitable for the subsequent chemical attachment of various molecules to the surface. In the present invention, the surface of a polymeric material which does not inherently carry suitable reactive groups can be activated by plasma surface treatment, plasma polymerization, or plasma polymerization followed by a subsequent plasma surface treatment.

SUMMARY OF INVENTION

Accordingly, in one aspect, the invention provides a novel composite material, especially a biomedical device, e.g. an ophthalmic device, such as a contact lens, with one or more wettable surfaces capable of holding a continuous layer of aqueous fluid thereon, characterized in that the composite comprises a carbohydrate which is covalently bound by a hydrolytically stable bond to a plasma surface prepared on the base material. Within the context of this invention a plasma surface prepared on a base, or bulk, material comprises either a plasma treated (or modified) surface on a base material or a plasma polymer coated to a base material. The base material is selected for it's bulk properties, such as mechanical strength, elasticity, gas permeability, optical clarity, to suit the intended application of the composite.

In a second aspect, the invention provides a biomedical product which provides enhanced comfort to the wearer, whereby said product is composed of a bulk material and a hydrophilic coating according to the first aspect of the invention. The hydrophilic coating consists of a carbohydrate attached covalently on to a plasma surface prepared on the bulk material, e.g. a thin, fully covering plasma polymer coating.

In a further aspect the invention provides a composite material, especially a biomedical device, e.g. an ophthalmic device, such as a contact lens, with one or more wettable surfaces capable of holding a continuous layer of aqueous fluid thereon characterized in that the composite comprises a carbohydrate which is covalently bound by a hydrolytically stable bond to reactive groups inherently present in the bulk material and at the surface of the biomedical device.

According to these aspects of the invention the carbohydrate is bound to the reactive groups either directly or via an oligofunctional compound having one or more functional groups capable of chemically reacting with the said reactive groups and having at least one additional functional group capable of chemically reacting with a carbohydrate to produce an activated surface.

In yet a further aspect, the invention provides a process for the manufacture of a wettable composite material, especially a biomedical device, e.g. an ophthalmic device, said process comprising the following steps:

1. exposing the non-composite biomedical device in its desired final form to a low pressure plasma in a vapor of at least one organic and/or inorganic compound under conditions whereby a thin film containing reactive groups is deposited on the desired surface(s) of the base material,
2. optionally, reacting the said reactive groups with an activating group, and/or with an oligofunctional compound having one or more functional groups capable of chemically reacting with the said reactive groups, or with the activated reactive groups, and having at least one additional functional group capable of chemically reacting with a carbohydrate to produce an activated surface,
3. optionally treating the carbohydrate with a reagent which modifies the said carbohydrate so that it is capable of reacting with the surface reactive or functional groups,
4. reacting the reactive groups or the functional groups with the carbohydrate,
5. optionally, treating the surface-immobilized carbohydrate with a reagent to stabilize the bond between the carbohydrate and the surface.

The resulting material is preferably washed and suitably packed ready for use.

In yet a further aspect, the invention provides a process for the manufacture of a wettable composite material, especially a biomedical device, e.g. an ophthalmic device, having reactive groups inherently (a priori) present in the bulk material, said process comprising the following step(s):

optionally, reacting the reactive groups inherently present in the bulk material of the non-composite biomedical device in its desired final form with an activating group, and/or with an oligofunctional compound having one or more functional groups capable of chemically reacting with the said reactive groups, or with the activated reactive groups, and having at least one functional group capable of chemically reacting with a carbohydrate to produce an activated surface, optionally treating the carbohydrate with a reagent which modifies the said carbohydrate so that it is capable of reacting with the surface reactive or functional groups, reacting the reactive groups or the functional groups with the carbohydrate, optionally, treating the surface-immobilized carbohydrate with a reagent to stabilize the bond between the carbohydrate and the surface.

The invention is therefore directed to a composite material, especially a biomedical device, e.g. an ophthalmic device, preferably a contact lens, with one or more wettable surfaces capable of holding a continuous layer of aqueous fluid thereon which composite material comprises a bulk material and a hydrophllic coating characterized in that the hydrophilic coating consists of a carbohydrate attached covalently to reactive groups at the surface of the bulk material, either directly or via functional groups of an oligofunctional compound, said oligofunctional compound in turn having functional groups being capable of reacting with said reactive groups at the surface of the bulk material and with the carbohydrate, wherein said reactive groups are either inherently (a priori) present in the bulk material or wherein said reactive groups have been attached to the surface of the bulk material by a plasma surface preparation, as hereinbefore defined, as well as to a process of manufacture of such a composite material.

The bulk material may be e.g. any material conventionally used for the manufacture of biomedical devices, e.g. contact lenses, which are not hydrophilic per se. Such materials are known to the skilled artisan and may comprise for example polysiloxanes, fluorinated (meth)acrylates or equivalent fluorinated comonomers derived e.g. from other polymerizable carboxylic acids, alkyl (meth)acrylates or equivalent alkyl comonomers derived from other polymerizable carboxylic acids, or fluorinated polyolefines, such as fluorinated ethylene propylene, or tetrafluoroethylene, preferably in combination with specific dioxols, such as perfluoro-2,2-diethyl-1,3-dioxol. Examples of suitable bulk materials are e.g. Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-diethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

The bulk material may also be e.g. any material conventionally used for the manufacture of biomedical devices, e.g. contact lenses, which are hydrophilic per se, since reactive groups, e.g. amine or hydroxy groups are inherently present in the bulk material and therefore also at the surface of a biomedical device manufactured therefrom. Such materials are known to the skilled artisan. Typical examples comprise e.g. Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon or Atlafilcon. Most of these materials are HEMA based, but suitable materials may also be based on other underlying monomers or polymers having reactive groups, e.g. hydroxy groups or amino groups, such as e.g. polyvinyl alcohol.

The bulk material may be any blood-contacting material conventionally used for the manufacture of renal dialysis membranes, blood storage bags, pacemaker leads or vascular grafts. For example, the bulk material may be a polyurethane, polydimethylsiloxane, polytetrafluoroethylene, polyvinylchloride or Dacron™.

Moreover, the bulk material may also be an inorganic or metallic base material with or without suitable reactive groups, e.g. ceramic, quartz, or metals, such as gold, or other polymeric or non-polymeric substrates. E.g. for implantable biomedical applications, ceramics, preferably coated with a polysaccharide, are very useful. In addition, e.g. for biosensor purposes, dextran coated base materials are expected to reduce nonspecific binding effects if the structure of the coating is well controlled. Biosensors may require polysaccharides on gold, quartz, or other non-polymeric substrates.

The reactive groups, inherently (a priori) present at the surface of the bulk material or having been introduced or attached to the surface of the bulk material by a plasma surface preparation, as hereinbefore defined, may be selected from a wide variety of groups well known to the skilled artisan. Typical examples are e.g. hydroxy groups, amino groups, carboxy groups, carbonyl groups, aldehyde groups, sulfonic acid groups, sulfonyl chloride groups, groups being replaceable by amino or hydroxy groups, such as halo groups, or mixtures thereof Amino groups and hydroxy groups are preferd.

Suitable organic or inorganic compounds for the plasma surface preparation step are e.g. ammonia, water vapor, carbon dioxide, carbon monoxide, noble gases, e.g. argon, oxygen, ozone or air, alcohols, amines or alkanones, preferably lower alkanols having up to eight carbon atoms, lower alkyl amines having up to eight carbon atoms, or lower alkanones having up to eight carbon atoms, e.g. methanol, ethanol, ammonia, methylamine, ethylamine, heptylamine, or acetone, or many other compounds known to those skilled in the art of plasma surface preparation. It is also within the scope of this invention to use mixtures of the compounds mentioned hereinbefore.

The first step of deposition of plasma polymer thin film coatings containing on their surfaces reactive groups such as amine and hydroxyl groups is fully described in the applicants International Patent Application PCT/AU89/00220 (Griesser et al.) and in Griesser H. J. and Chatelier R. C. Journal of Applied Polymer Science: Applied Polymer Symposium 46, 361–384 (1990);

Suitable activating compounds for the optional step 2 are e.g. anhydrides or activated esters, such as 2,2,2-trifluoroethanesulphonyl chloride, p-toluenesulphonyl chloride, cyanogen bromide or p-nitrophenylesters.

Suitable oligofunctional compounds for the optional step 2 have preferably up to four functional groups and are, more preferred, bifunctional. Preferred bifunctional compounds for step 2 are preferably epihalohydrins, bis-oxiranes or diisocyanates. Typical examples are e.g. the diglycidyl ether of bisphenol A, 1,3-butadiene diepoxide or the diglycidyl ether of 1,4-butanediol. These bifunctional compounds yield an activated surface with pendant epoxy groups, halogen groups or isocyanato groups. However, the present invention is not limited to the use of epoxy, halogen or isocyanato groups as functional groups. Many other oligo- or bifunctional reactive compounds can effect the desired covalent crosslinking between a reactive group rich coating, e.g. a hydroxyl or amine rich coating, and a carbohydrate. For example, other suitable bifunctional compounds are diacid chlorides, ditosylates, dihydrazides and any compound which contains more than one functional group which can react with the reactive groups as hereinbefore defined. A preferred embodiment of the invention is the use of epihalohydrins, bis-oxiranes (diglycidyl ethers) or diisocyanates as oligofunctional compounds. It is further preferred that said oligofunctional compounds, or in the preferred case the bifunctional compounds, have different reactivity with respect to their functional groups, or to their two functional groups, respectively.

Suitable epihalohydrins are e.g. epichlorohydrine or methylepichlorohydrin.

One class of bis-oxirane compounds comprises diglycidyl compounds of formula I

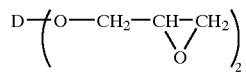

(I)

wherein D is an organic divalent radical and wherein each of the glycidyloyxy groups are covalently bonded to a carbon atom of D. Preferably the compounds of formula I are polyglycidyl ethers or carboxylate esters.

The organic radical D may be aliphatic, heterocyclic, aromatic, or araliphatic which is bound to the glycidyl oxygen directly or through a carbonyl group.

In one preferred embodiment D is aliphatic. Especially suitable radicals include alkylene of up to 25 carbon atoms, or said alkylene interrupted by one or more hetero atoms, such as oxygen, or cyclohexylene. More preferably, D is alkylene of 2 to 6 carbon atoms, or —$C_2$–$C_4$-alkylene(O—$C_2$–$C_4$-alkylene)$_p$ where p is 1 to 8. Also especially suitable are the aforementioned aliphatic radicals terminating in carbonyl groups to form the corresponding diglycidyl carboxylate ester.

In another preferred embodiment D is aromatic. Especially suitable aromatic radicals include phenyl, biphenyl, phenyl-lower alkylene-phenyl, phenyloxyphenyl, or phenylsulfonylphenyl, which are further unsubstituted or are substituted by lower alkyl, lower alkoxy, or halo.

The term "lower", whenever used in the context of this invention and if not defined otherwise, defines groups having up to seven carbon atoms, preferably groups having up to four carbon atoms. Thus, for the reason of illustration, e.g. lower alkyl is alkyl having up to 7 carbon atom, such as methyl, ethyl, propyl, butyl, or hexyl, and lower alkoxy is alkoxy having up to 7 carbon atoms, such as methoxy, ethoxy, butoxy, or heptyloxy.

Another class of bis-oxirane compounds comprises polyglycidyl compounds of the formula II

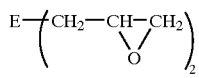

(II)

wherein E is an organic divalent radical and wherein each of the glycidyl radicals are covalently bonded to a nitrogen or carbon atom of E. Preferably E is aliphatic, aromatic, heterocyclic or araliphatic, as hereinbefore defined for radical D.

In a preferred subembodiment E is a bivalent hydantoin radical which is bound to the glycidyl groups through the respective nuclear nitrogen atoms, and said hydantoin is otherwise unsubstituted or substituted by lower alkyl.

In an alternate preferred subembodiment E is alkylene of up to 6 carbon atoms.

A third class of bis-oxirane compounds are those of the formula III

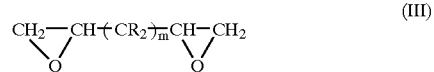

(III)

wherein m is 0, 1 or 2 and each R independently represents hydrogen or lower alkyl.

Also mixtures of the above bis-oxiranes of formulae I, II and III may be employed. Suitable bis-oxiranes, most of which are readily available and all of which are known, and which can be used according to this invention, have been disclosed e.g. in U.S. Pat. No. 4,598,122.

Suitable bis-oxiranes are e.g. the diglycidyl ether of bisphenol A, 1,3-butadiene diepoxide or the diglycidyl ether of 1,4-butanediol, divinylbenzene dioxide, diglycidyl ether, limonene dioxide, vinylcyclohexene dioxide, the diglycidyl ether of bisphenol F, 3,4-epoxycyclohexylmethyl 3,4-epoxycyclohexane carboxylate, phthalic acid diglycidyl ester, diglycidyl aniline, or oligoethyleneoxide diclycidylethers, such as di(ethyleneglycol) diglydicyl ether, tetra(ethyleneglycol) diglycidyl ether, or octa(ethyleneglycol) diglycidyl ether.

Suitable diisocyanates are generally aromatic, aliphatic or cycloaliphatic diisocyanates, or mixtures thereof. The aromatic moiety thereof is preferably phenyl, naphthyl or anthryl, which are unsubstituted or substituted by alkyl having up to four carbon atoms, by alkoxy having up to four carbon atoms or by halo, preferably chloro, wherein two aromatic moieties may be connected by an ether bond or by an alkenylene group of up to four carbon atoms, the aliphatic moiety thereof is preferably alkyl having up to 10 carbon atoms, the cycloaliphatic moiety thereof is preferably cycloalkyl or bicycloalkyl having up to 6 carbon atoms in each cycloalkyl ring.

Examples of such diisocyanates are toluene-2,4-diisocyanate, toluene-2,6-diisocyanate, isophorone diisocyanate, ethylene diisocyanate, ethylidene diisocyanate, propylene-1,2-diisocyanate, cyclohexylene-1,2-diisocyanate, cyclohexylene-1,4-diisocyanate, m-phenylene-1,2-diisocyanate, 3,3'-diphenyl-4,4'-biphenylene diisocyanate, 4,4'-biphenylene diisocyanate, 4,4'-diphenylmethane diisocyanate, 3,3'-dichloro-4,4'-biphenylene diisocyanate, 4,4'-diphenyl diisocyanate, 1,6-hexamethylene diisocyanate, 2,2,4-trimethyl-hexamethylene diisocyanate, 1,4-tetramethylene diisocyanate, 1,10-decamethylene diisocyanate, cumene-2,4-diisocyanate, 1,5-naphthalene diisocyanate, methylene dicyclohexyl diisocyanate, 1,4-cyclohexylene diisocyanate, p-tetramethyl xylylene diisocyanate, p-phenylene-1,4-diisocyanate, 4-methoxy-1,3-phenylene diisocyanate, 4-chloro-1,3-phenylene diisocyanate, 4-bromo-1,3-phenylene diisocyanate, 4-ethoxy-1,3-phenylene diisocyanate, 2,4-dimethyl-1,3-phenylene diisocyanate, 5,6-dimethyl-1,3-phenylene diisocyanate, 2,4-diisocyanatodiphenylether, 4,4'-diisocyanatodiphenylether, benzidine diisocyanate, 4,6-dimethyl-1,3-phenylene diisocyanate, 9,10-anthracene diisocyanate, 4,4'- diisocyanatodibenzyl, 3,3'-dimethyl-4,4'-diisocyanatodiphenylmethane, 2,6dimethyl-4,4'-diisocyanatodiphenyl, 2,4-diisocyanatostilbene, 3,3'-dimethoxy-4,4'-diisocyanatodiphenyl, 1,4-anthracene diisocyanate, 1,8-naphthalene diisocyanate, 1,3-bis-isocyanatomethyl-cyclohexane, or 4,4'-(dicyclohexyl) methane diisocyanate.

Preferred are diisocyanates having different reactivity with respect to their two NCO groups, such as isophorone diisocyanate, 2,4-toluene diisocyanate, or 2,2,4-trimethylhexamethylene diisocyanate.

Suitable carbohydrates according to this invention comprise natural products, modified carbohydrates and synthetic carbohydrates. Examples for these groups of carbohydrates are sugars, such as monosaccharides, di- and oligosaccharides, cyclic oligosaccharides, linear polysaccharides, whether homopolysaccharides or heteropolysaccharides, branched polysaccharides, segmented polysaccharides, lipopolysaccharides, glycoproteins and proteoglycans. The modified products or synthetic products may be modified e.g. by oxidation, etherification or esterification, they may further comprise functional groups such as aldehyde groups, acetal groups, ketal groups, acylamino groups, preferably acetylamino groups, anhydro groups or lactone groups. They may further have groups which may be charged, such as —$NH_2$, —COOH, —$OSO_3H$, or —$OP(O)(OH)_2$.

Examples of suitable carbohydrates are known to the skilled artisan and can be found in conventional textbooks, or monographs. The following listing is exemplary only and not meant to restrict the invention:

Suitable sugars are e.g. glucosamin, galaktosamin, neuraminic acid, muraminic acid, sialinic acid, L-fucose, arabinose, xylose, glucuronic acid, gluconic acid or levoglucosan.

Suitable oligosaccarides are e.g. lactose, maltose, cellobiose, chitohexanose, trehalose, isomaltulose, leucrose.

Suitable polysaccharides and derivatives are e.g. hyaluronic acid, deacylated hyaluronic acid, chitosan, chitin 50, fucoidan, carrageenans, dextran, blue dextran, aminated dextran, galaktomannan, glucomannan, pullulan, glycosaminoglycan, heparin, agarose, curdlan, pectin, pectic acid, xanthan, hydroxypropyl cellulose or chitosan, carboxymethyl cellulose or chitosan, emulsan, laminaran, inulin, pustulan, scleroglucan, schizophyllan, or mucopolysaccharides.

Further examples of suitable carbohydrates are D-ribose, L-arabinose, D-xylose, L-fucose, D-mannose, D-galactose, D-glucosamine, muramic acid, D-galactosamine; . D-gluocoronic acid, D-mannuronic acid, D-galacturonic acid, L-glycero-D-manno-heptose, neuraminic acid. Further examples of polysaccharides are agarose, alginates, carrageenan, cellulosics, such as acetate, carboxymethyl, ethyl, hydroxyethyl, hydroxypropyl, hydroxypropylmethyl, methyl cellulose, chitin/chitosan, dextran, furcellaran, gellan gum, guar gum, gum arabic, heparin, hyaluronic acid, hydroxypropyl guar, karaya gum, laminaran, locust bean gum, pectin (low or high methoxyl), rhamsan gum, starches, tragacant gum, welan gum, xanthan gum.

Examples of especially suitable monosaccharides include glycerol, threose, glucose, galactose and fructose. Examples of especially suitable oligosaccharides include sucrose, maltose, lactose and cellobiose. Examples of especially suitable polysaccharides include dextrans, starches, dextrins, glycogens, inulin, glycosaminoglycans and mucopolysaccharides, further preferred are dextran, chitosan, hyaluronic acid, mucin, fucoidan, and glucosamin.

Naturally occurring carbohydrates may be modified in order to enhance their reactivity with activated surfaces. For example, oxidation of dextran with periodate yields aldehydes which can react with amines on the surface of the material; treatment of dextran with bromoacetic acid in alkaline solution places pendant carboxymethyl groups on the polysaccharide backbone which, in turn, can form ester or amide links with surface hydroxyls or amines, respectively; treatment of dextran with choroethylamine in alkaline solution places pendant aminomethyl groups on the polysaccharide backbone which, in turn, can react with surface epoxy, acid chloride or tosylate groups.

Step two may be performed by immersing the plasma treated material in a solution or vapour of oligo- or bifunctional compound. For example, the surface may be immersed in a solution of 0.1–5.0 ml epichlorohydrin (preferably 0.2–2.0 ml), and 10–100 ml of 0.4 ml of 0.4 M sodium hydroxide (preferably 20–30 ml) in 10–100 ml of diethylene glycol dimethyl ether (preferably 20–30 ml) for 1–6 hours (preferably 4–6 hours) at 10–60° C. (preferably 20–30° C.). Alternatively, the surface may be immersed in a solution containing 20 ml water, 0.4 ml 1,4-butanediol diglycidylether, and 1 ml benzyltrimethylammonium hydroxide at 60° C. for 5 hours. The sample is then rinsed with water at room temperature.

The reaction between the carbohydrate and the reactive groups of the surface is performed in such a way that a highly water retaining carbohydrate layer is provided on the outermost surface of the novel composite material. Preferably the material with an activated surface is placed in a solution of carbohydrate for an appropriate time. For example the method described by S. Lofas and B. Johnsson in J. Chem. Soc.: Chem. Commun. 1526 (1990) may be used. Thus the surface can be reacted with 0.1–15.0 g (preferably 2.0–5.0 g) of dextran (molecular weight 1,000–5,000,000 Da, preferably 500,000–2,000,000 Da) in 10–50 ml (preferably 20–30 ml) of 0.01–5.0 M (preferably 0.1–2.0 M) sodium hydroxide for 0.1–48 hours (preferably 20–25 hours) at 10–60° C. (preferably 20–30° C.). Excess dextran is washed off by rinsing the sample in distilled water. Alternatively, the material may be immersed in a solution containing 20 ml water, 0.2 g dextran (molecular weight 1,000 to 40,000,000 Da (preferably 500,000 to 40,000,000 Da) and 1 ml benzyltrimethylammonium hydroxide at 60° C. for 18 hours. Again, excess dextran is washed off by rinsing the sample in distilled water.

The invention encompasses all such methods and the biomedical devices, e.g. ophthalmic devices so obtained.

The biomedical devices of the inventions are e.g. implantable biomedical devices, such as prostheses, vascular grafts, catheters, pacemakers or shunts, or ophthalmic devices. The ophthalmic device of the invention is e.g. a contact lens, an eye bandage or an intraocular lens, and preferably it is a contact lens.

In its broadest aspects the invention is directed to a composite material, especially a biomedical device, e.g. an ophthalmic device, preferably a contact lens, with one or more, preferably one or two, wettable surfaces capable of holding a continous layer of aqueous fluid thereon which composite material comprises a bulk material and a hydrophilic coating characterized in that the hydrophilic coating consists of a carbohydrate, including a modified carbohydrate, attached covalently to reactive groups at the surface of the bulk material, either directly or via functional groups of an oligofunctional compound, said oligofunctional compound in turn having functional groups being capable of reacting with said reactive groups at the surface of the bulk material and with the carbohydrate, wherein said reactive groups are either inherently (a priori) present in the bulk material or wherein said reactive groups have been attached to the surface of the bulk material by a plasma surface preparation.

A preferred subembodiment of the invention is a biomedical device, e.g. an ophthalmic device wherein reactive groups are inherently present in the bulk material and wherein the oligofunctional compound is a bis-oxirane or an epihalohydrin, preferably a bis-oxirane.

A further preferred subembodiment of the invention is a biomedical device, e.g. an ophthalmic device wherein reactive groups are inherently present in the bulk material, wherein the oligofunctional compound is a bis-oxirane and the carbohydrate is a polysaccharide. Said carbohydrate is preferably selected from dextran, chitosan, hyaluronic acid, mucin, fucoidan, and glucosamin.

A further preferred subembodiment of the invention is a biomedical device, e.g. an ophthalmic device wherein reactive groups are inherently present in the bulk material, wherein the oligofunctional compound is a diisocyanate and the carbohydrate is a non-polysaccharide carbohydrate.

A further preferred subembodiment of the invention is a biomedical device, e.g. an ophthalmic device wherein reactive groups are inherently present in the bulk material, wherein the oligofunctional compound is a diisocyanate and the carbohydrate is dextran.

An additionally preferred subembodiment of the invention is a biomedical device, e.g. an ophthalmic device wherein reactive groups are inherently present in the bulk material, and wherein the oligofunctional compound has different reactivity with respect to its functional groups. Such an oligofunctional compound may be e.g. a bis-oxirane having different reactivity with respect to its two functional groups, such as for example limonene dioxide, vinylcyclohexene dioxide, 3,4-epoxycyclohexylmethyl 3,4-epoxycyclohexane carboxylate, or it may be e.g. a diisocyanate having different reactivity with respect to its two functional groups, such as for example isophorone diisocyanate, 2,4-toluene diisocyanate, or 2,2,4-trimethylhexamethylene diisocyanate.

Another preferred embodiment of the invention is a biomedical device, e.g. an ophthalmic device wherein said reactive groups have been attached to said surface by a plasma surface preparation and wherein the oligofunctional compound is selected from an epihalohydrin, bis-oxirane, diisocyanate, diacid chloride, and ditosylate.

Within this embodiment it is preferred that the oligofunctional compound is a bis-oxirane. It is further preferred that the oligofunctional compound is a bis-oxirane having different reactivity with respect to its two functional groups.

Another preferred embodiment of the invention is a biomedical device, e.g. an ophthalmic device wherein said reactive groups have been attached to said surface by a plasma surface preparation and wherein the oligofunctional compound is a bis-oxirane and the carbohydrate is a polysaccharide, which is preferably selected from dextran, chitosan, hyaluronic acid, mucin, fucoidan, and glucosamin.

Another preferred embodiment of the invention is a biomedical device, e.g. an ophthalmic device wherein said reactive groups have been attached to said surface by a plasma surface preparation and wherein the oligofunctional compound is a diisocyanate. It is further preferred that the oligofunctional compound is a diisocyanate having different reactivity with respect to its two functional groups.

Another preferred embodiment of the invention is a biomedical device, e.g. an ophthalmic device wherein said reactive groups have been attached to said surface by a plasma surface preparation and wherein the oligofunctional compound is a diisocyanate and the carbohydrate is a polysaccharide, which is preferably selected from dextran, chitosan, hyaluronic acid, mucin, fucoidan, and glucosamin.

A further preferred subembodiment of the invention is a biomedical device, e.g. an ophthalmic device wherein reactive groups are inherently present in the bulk material, wherein the carbohydrate is a polysaccharide which is directly bonded to the reactive groups. Said carbohydrate is preferably selected from dextran, chitosan, hyaluronic acid, mucin, fucoidan, and glucosamin.

A further preferred subembodiment of the invention is a biomedical device, e.g. an ophthalmic device wherein reactive groups are inherently present in the bulk material, wherein the carbohydrate is a non-polysaccharide carbohydrate which is directly bonded to the reactive groups.

A further preferred subembodiment of the invention is a biomedical device, e.g. an ophthalmic device wherein reactive groups are inherently present in the bulk material, wherein the carbohydrate is dextran which is directly bonded to the reactive groups.

Another preferred embodiment of the invention is a biomedical device, e.g. an ophthalmic device wherein said reactive groups have been attached to said surface by a plasma surface preparation and wherein the carbohydrate is a polysaccharide, which is directly bonded to the reactive groups. Said carbohydrate is preferably selected from dextran, chitosan, hyaluronic acid, mucin, fucoidan, and glucosamin.

Another preferred embodiment of the invention is a biomedical device, e.g. an ophthalmic device wherein said reactive groups which have been attached to said surface by a plasma surface preparation are hydroxy or amino groups and wherein the carbohydrate which is directly bonded to the reactive groups is preferably selected from dextran, chitosan, hyaluronic acid, mucin, fucoidan, and glucosamin, and is most preferably dextran.

The biomedical devices, e.g. ophthalmic devices according to the present invention have a variety of unexpected advances over those of the prior art which make those devices, especially contact lenses, according to the invention very suitable for practical purposes, e.g. as contact lenses for extended wear. For example, they do have a high surface wettability which can be demonstrated by their contact angles, their water retention and their water-film break up time or tear film break up time. The water retention time is closely related to the water-film break up time ("BUT") and the tear film break up time, in that a high water retention time results in a high water-film break up time or tear film break up time.

In addition the biomedical devices, e.g. ophthalmic devices, such as contact lenses according to this invention have a very pronounced biocompatibility combined with good mechanical properties. For example, there are generally no adverse eye effects observed, while the adsorption of proteins or lipids is low, also salt deposit formation is lower than with conventional contact lenses. Generally one may state that there is low fouling, low microbial adhesion and low bioerosion while the good mechanical properties can be for example found in a low friction coefficient and low abrasion properties.

In summary the ophthalmic devices according to this invention, such as contact lenses, provide a combination of low spoilation with respect to cell debris, cosmetics, dust or dirt, solvent vapors or chemicals, with a high comfort for the patient wearing such contact lenses in view of the soft hydrogel surface which for example provides a very good on-eye movement of the contact lenses.

The biomedical devices (e.g. renal dialysis membranes, blood storage bags, pacemaker leads or vascular grafts) resist fouling by proteins by virtue of the continuous layer of bound water, thus reducing the rate and extent of thrombosis. Blood-contacting devices fabricated according to the present invention are therefore haemocompatible and biocompatible.

Further preferred embodiments are apparent to the skilled artisan from the disclosure and the examples. However, the examples are illustrative only and are not intended to limit the disclosure whatsoever.

Hereinafter two possible reaction schemes are shown whereby epoxy groups may be covalently attached onto a plasma treated biomedical device, e.g. a contact lens:

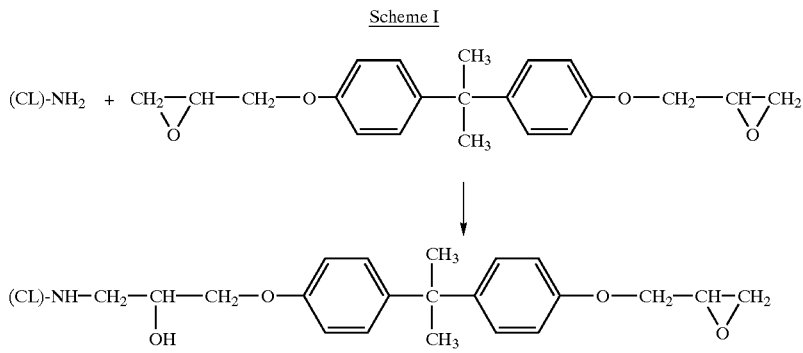

Scheme I

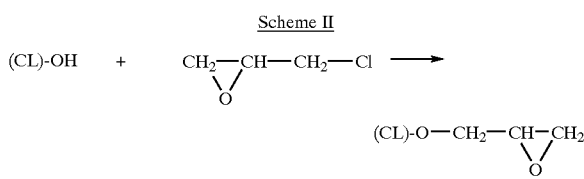

Scheme II wherein (CL) denotes the surface of a contact lens, (CL)—$NH_2$ denotes an exemplary amino group present at the surface of said contact lens and (CL)—OH denotes an exemplary hydroxy group present at the surface of said contact lens.

A further reaction scheme shows the covalent attachment of a carbohydrate onto epoxy groups bonded to a biomedical device, e.g. a contact lens:

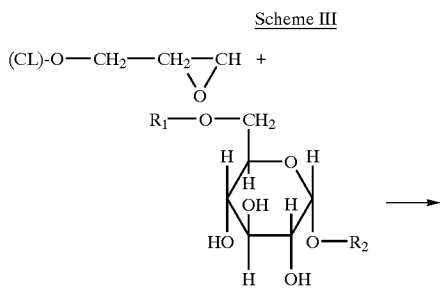

Scheme III

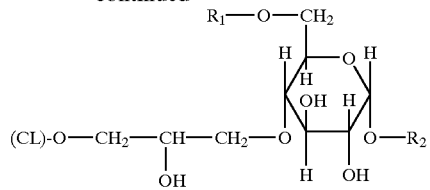

-continued wherein (CL) denotes the surface of a contact lens, and $R_1$ and $R_2$ have the meaning of a conventional residue extending the chain of a carbohydrate.

Where the carbohydrate contains a trans vicinal diol the carbohydrate, such as e.g. dextran, may be oxidized in part with an appropriate oxidizing agent, e.g. with sodium periodate, in order to obtain ring cleavage and formation of aldehyde functions. Said aldehyde functions may be reacted with amino groups, present as reactive groups or as functional groups at the surface of the biomedical device, to form an —N=CH-group. Said groups may be reduced with a suitable reducing agent to a hydrolytically stable —NH—$CH_2$-group linking the carbohydrate molecule to the device surface.

Without limiting the invention, further combinations of chemical groups which may be reacted with each other in order to obtain composite materials according to this invention are e.g. as follows: A carbonyl reactive group at the surface of the device is reacted with a hydrazide functional group of a dihydrazide while the other hydrazide functional group thereof is reacted with an aldehyde group of a carbohydrate. An aldehyde reactive group at the surface of the device is reacted with an amino group of a carbohydrate, and reduced if desire&. An amino reactive group or a hydroxy reactive group at the surface of the device is reacted with an epoxide functional group of a diepoxide while the other epoxide functional group thereof is reacted with an amino or hydroxy group of a carbohydrate. An amino reactive group or a hydroxy reactive group at the surface of the device is reacted with one functional end group of an epichlorohydrin while the other functional end group thereof is reacted with an amino or hydroxy group of a carbohydrate. An amino reactive group or a hydroxy reactive group at the surface of the device is reacted with an isocyanato functional group of a diisocyanate while the other isocyanato functional group thereof is reacted with an amino or hydroxy group of a carbohydrate. A carboxy group at the surface of the device is reacted with an amino group of a carbohydrate. A reactive group at the surface of the device which is replaceable by an amino or hydroxy group is replaced by an amino or hydroxy group of a carbohydrate.

In the examples, if not otherwise indicated, temperatures are given in degrees Celsius, and contact angles are given in degrees.

EXAMPLE 1 (COMPARATIVE)

Commercially available fluoropolymer (Fluorofocon A™) contact lenses are removed from storage in saline solution, rinsed with distilled water and inserted for in vivo testing (with unpreserved, buffered saline solution). Each lens is fitted to a subject who is unadapted to contact lens wear. Subjects are chosen to whom the lenses could be adequately fitted. The measured variables are: (1) overall wettability, (2) front surface break up time (FS BUT), (3) speed of surface drying, (4) surface coverage. The variables are assessed immediately after insertion and again ten minutes after insertion.

EXAMPLE 2 (COMPARATIVE)

Commercially available silicone elastomer (Elastofilcon A™) contact lenses are removed from storage in saline solution, rinsed with distilled water and then allowed to dry in air prior to measurement of air/water contact angles.

Contact angles are measured using a modified Kernco-G2 contact angle goniometer. By placing the sample on a flat stage and placing a drop of distilled water on the apex of the anterior lens surface using a micrometer driven syringe, and then aligning rotatable cross hairs in the eyepiece at a tangent to the curvature of the lens and the drop at the water/air/lens interface, the sessile contact angle (SCA) can be measured. The micrometer driven syringe is then used to gradually increase the volume of the drop by injecting more water into it, just until the drop begins to advance across the surface, at which point the advancing contact angle (ACA) is measured using the rotatable crosshairs. The micrometer driven syringe is then used to gradually decrease the volume of the drop by withdrawing water from it, until the drop begins to recede across the surface, at which point the receding contact angle (RCA) is measured.

EXAMPLE 3

Commercially available RGP fluoropolymer (Fluorofocon A™) contact lenses are coated with a thin polymer film produced by plasma polymerization of methanol vapour at a pressure of 0.7 torr, input power of 10 watts, signal frequency of 300 kHz and treatment time of 1 minute.

The plasma modified contact lenses are reacted with 0.235 ml of epichlorohydrin in a mixture of 25 ml of 0.4 M NaOH and 25 ml of diethylene glycol dimethyl ether at 20° C. for 4 hours. The lenses are then washed 3 times in distilled water, twice with ethanol and again 3 times in distilled water.

Dextran is attached to the epichlorhydrin treated lens surfaces by soaking in a solution of 3.0 g Dextran dissolved in 25 ml of 0.1 M NaOH for 20 hours. The lenses are then washed 5 times in distilled water and allowed to dry in air before measuring contact angles. The treated lenses are then stored in saline solution before testing under identical conditions as example 1.

The in vitro data in Table 1 reveal a decrease in sessile, advancing and receding air/water contact angles of the contact lenses when the surfaces are treated according to this invention.

The in vivo data in Table 2 reveal an increase in wettability by tear film when the surfaces are treated according to this invention.

EXAMPLE 4

Example 4 is identical to Example 3, except that the contact lenses are commercially available silicone elastomer (Elastofilcon A™) contact lenses, and measurements of air/water contact angles are made after rinsing with distilled water and allowed to dry in air. The results in Table 1 reveal a decrease in sessile, advancing and receding air/water contact angles of the contact lenses when the surfaces are treated according to this invention.

Brief Description of Tables 1 and 2

Table 1 shows the change in air/water contact angles consequent on attachment of polysaccharide onto the surface of RGP fluoropolymer (Fluorofocon A™) and silicone elastomer (Elastofilcon A™) contact lenses.

Table 2 shows the effect of grafted polysaccharide on the time taken for the contact lens to dry, for RGP fluoropolymer (Fluorofocon A™) contact lenses.

TABLE 1

| Contact Lens | SCA* | ACA* | RCA* |
|---|---|---|---|
| Fluorofocon A ™ lenses: | | | |
| Untreated lenses | 111 | 119 | 47 |
| Lenses with Dextran (MW = 500,000) | 90 | 95 | 9 |
| Lenses with Dextran (MW = 2'000,000) | 80 | 85 | 4 |
| Elastofilcon A ™ lenses: | | | |
| Untreated lenses | 102 | 107 | 61 |
| Lenses with Dextran (MW = 500,000) | 99 | 104 | 45 |
| Lenses with Dextran (MW = 2'000,000) | 93 | 99 | 17 |

*SCA, ACA and RCA are the sessile, advancing and receding air/water contact angles respectively.

TABLE 2

| | Initially | | After 10 minutes | |
|---|---|---|---|---|
| Variable | Example 3 | Comparative example 1 | Example 3 | Comparative example 1 |
| Wettability* | 3.5 +/− 0.9 | 2.5 +/− 1.3 | 3.3 +/− 0.6 | 1.9 +/− 0.7 |
| FS BUT# (secs) | 10 +/− 3 | 7 +/− 4 | 9 +/− 2 | 5 +/− 2 |
| Speed of drying+ | 1.4 +/− 0.6 | 2.1 +/− 0.7 | 1.3 +/− 0.4 | 2.9 +/− 0.2 |

Wettability*
0 = surface completely non-wetting
1 = very thin tear layer, fast break up time (BUT)
2 = moderately thin layer, fast BUT
3 = tear layer slightly thin, BUT approximately equal to interblink interval
4 = tear layer thick and smooth, no dry patches, BUT greater than interblink interval
FS BUT#
Front surface break up time
Speed of drying+
1 = slow
2 = moderate
3 = fast

EXAMPLE 5 (COMPARISON)

An important criterion for the usefulness of the present invention is the time taken for water to recede from 50% of the surface of a substrate, such as a contact lens. This parameter is abbreviated "WRT" and presented in seconds in this example and hereinafter. The bulk material used is fluorinated ethylene propylene. This material, without modification of its surface has a WRT of <1 second.

EXAMPLE 6

A flat substrate of fluorinated ethylene propylene is subjected to a plasma treatment in the presence of heptylamine.

1 g of polysaccharide in 200 ml water is treated with 3 g NaIO$_4$ and reacted with the plasma treated substrate having amino groups at its surface in the presence of NaCNBH$_3$ at a pH of 6 to 9. A substrate with a hydrophilic coating is obtained for which the following time taken for water to recede from 50% of the surface (WRT) is measured:

|  | polysaccharide | MW (kDa) | WRT (sec) |
|---|---|---|---|
| a) | dextran | 9.3 | 180 |
| b) | dextran | 74.2 | 180 |
| c) | dextran | 515 | 180 |
| d) | dextran | 2000 | 180 |
| e) | blue dextran | 2000 | 180 |
| f) | pectic acid | n.d. | 180 |
| g) | polyquat JR30M | n.d. | 90 |

EXAMPLE 7

A flat substrate of fluorinated ethylene propylene is subjected to a plasma treatment in the presence of methanol. The substrate having hydroxy groups at its surface is treated with 1,4-butanediol diglycidyl ether in the presence of benzyltrimethylammonium hydroxide and with dextran. A substrate with a hydrophilic coating is obtained for which the following time taken for water to recede from 50% of the surface (WRT) is measured:

|  | polysaccharide | MW (kDa) | WRT (sec) |
|---|---|---|---|
| a) | dextran | 515 | 75 |
| b) | dextran | 2000 | 90 |
| c) | dextran | 2000 | 210 |
| d) | dextran | 5–40000 | >300 |

In the following examples 1,4-butanediol diglycidyl ether is replaced by di(ethyleneglycol)diglycidyl ether (example e), by tetra(ethyleneglycol)diglycidyl ether (example f) or by octa(ethyleneglycol)diglycidyl ether (example g):

| e) | dextran | 2000 | 150 |
|---|---|---|---|
| f) | dextran | 2000 | 90 |
| g) | dextran | 2000 | 135 |

EXAMPLE 8

An Elastofilcon contact lens is subjected to a plasma treatment in the presence of heptylamine. Dextran with a molecular weight (MW) of 74.2 kDa is treated with NaIO$_4$/NaCNBH$_3$ and reacted with the plasma treated contact lens having amino groups at its surface. A contact lens with a hydrophilic coating is obtained for which a time taken for water to recede from 50% of the surface (WRT) of 180 seconds is measured.

EXAMPLE 9

A Tefilcon contact lens is subjected to a plasma treatment in the presence of heptylamine. Dextran with a molecular weight (MW) of 74.2 kDa is treated with NaIO$_4$/NaCNBH$_3$ and reacted with the plasma treated contact lens having amino groups at its surface. A contact lens with a hydrophilic coating is obtained for which a time taken for water to recede from 50% of the surface (WRT) of 90 seconds is measured. By contrast, a Tefilcon contact lens, without modification of its surface, has a WRT of 10 seconds.

EXAMPLE 10

A flat substrate of a) polyurethane, b) glass and c) Al-Kapton is subjected to a plasma treatment in the presence of heptylamine. A polysaccharide is treated with NaIO$_4$/NaCNBH$_3$ and reacted with the plasma treated substrate having amino groups at its surface. A substrate with a hydrophilic coating is obtained for which the following time taken for water to recede from 50% of the surface (WRT) is measured:

|  | polysaccharide | MW (kDa) | WRT (sec) |
|---|---|---|---|
| a) | dextran | 74.2 | 900 |
| b) | dextran | 74.2 | 120 |
| c) | dextran | 74.2 | 120 |

EXAMPLE 11

A silicone film, made from UV-cured silicone PS 2067 (Hüls America Inc, Bristol, USA) by casting it on a Folanorm foil (Foex®, Zürich, Switzerland) and irradiation, is placed in an RF-GDP system (radio frequency glow discharge plasma) and the system is evacuated to 0.1 mbar. The film is exposed at a pressure of 0.1 mbar to an oxygen plasma at a power of about 40 W, at an oxygen flow of 10 nanocubic centimeters for 30 seconds, thereafter to air with release of the vacuum.

EXAMPLE 12

A polybutadiene film, made from a tetrahydrofuran solution of poly(1,2-syndiotactic butadiene)(Polysciences, Inc., cat #16317) by casting said solution on a Folanorm foil and evaporating the tetrahydrofuran under a nitrogen flow, is modified by the method described in example 11.

EXAMPLE 13

The plasma treated silicone film of example 11 is placed into a desiccator over about 5 ml of 2,4-tolylene diisocyanate (2,4-TDI). The desiccator is heated to 50° C. and evacuated to 0.008 mbar. The reaction with 2,4-TDI vapors is carried out for 2.5 hours. After cooling to room temperature the film is taken off, washed vigorously with dry acetone and soaked in a DMSO solution (comprising 5% LiCl) of chitosan for 8 hours. The modified film is washed thereafter 24 hours with water, dried and analyzed.

EXAMPLE 14 to 16

The following films are treated according to the method of example 13 except where specified otherwise:

Example 14: The oxygen plasma treated polybutadiene film of example 12. Time of vapor reaction is 2.5 hours.

Example 15: A poly(hydroxyethyl methacrylate) (p-HEMA) film made from a solution consisting of HEMA (92%), ethylene glycol dimethacrylate (5%) and, as a photoinitiator, Irgacure 184 (3%) by casting it on a Folanorm foil and UV-irradiation. Time of vapor reaction is 6 hours. Time of reaction with chitosan is only 30 minutes.

Example 16: A polyvinyl alcohol film (PVA) made from a DMSO solution of PVA 72 000 (Fluka AG) (99%) and isophorone diisocyanate (IPDI), (Aldrich) (1%) by casting it on a Folanorm foil and heating to 70° C. for 2 hours under reduced pressure. Time of vapor reaction is 6 hours. Time of reaction with chitosan is only 30 minutes.

The following table lists the contact angles ("CA"), measured with a system G 40 (Krüss GmbH, Hamburg Germany), of the polymeric films before treatment and after treatment:

| Example | Material | CA before treatment (°) | CA after treatment (°) |
|---|---|---|---|
| 13 | silicone | 100.4 | 56.9 |
| 14 | polybutadiene | 79.5 | 52.5 |
| 15 | p-HEMA | 78.4 | 67.5 |
| 16 | PVA | 47.1 | 31.5 |

EXAMPLE 17 to 20

Examples 13 to 16 are repeated with the same 2,4-TDI vapor modified films, but using, instead of the step of soaking in a chitosan solution, the step of soaking in a 1% solution of hyaluronic acid, comprising about 1 mg of catalyst (DBTDL), in DMSO. The hyaluronic acid is obtained from Czechoslovakia (Product ZD Straznice, CSFR).

The following table lists the contact angles ("CA"), measured with a system G 40 (Krüss GmbH, Hamburg Germany), of the polymeric films before treatment and after treatment:

| Example | Material | CA before treatment (°) | CA after treatment (°) |
|---|---|---|---|
| 17 | silicone | 100.4 | 57.0 |
| 18 | polybutadiene | 79.5 | 68.0 |
| 19 | p-HEMA | 77.8 | 58.3 |
| 20 | PVA | 47.1 | 42.1 |

EXAMPLE 21 to 24

Polymeric films as described in examples 13 to 16 are soaked in a 5% 2,4-TDI solution in a solvent incapable to swell the polymer (for solvent information see table hereinafter). The reactions are carried out at room temperature, under nitrogen gas for 12 hours. After reaction the films are washed in acetone and dried under reduced pressure. The films are thereafter soaked in a 1% DMSO solution (comprising 5% LiCl) of chitosan for 24 hours. The modified films are washed thereafter for 24 hours with distilled water, dried and analyzed.

The following table lists the contact angles ("CA"), measured with a system G 40 (Krüss GmbH, Hamburg Germany), of the polymeric films before treatment and after treatment:

| Example | Material (Solvent) | CA before treatment (°) | CA after treatment (°) |
|---|---|---|---|
| 21 | silicone (DMSO) | 100.4 | 59.8 |
| 22 | polybutadiene (DMSO) | 79.5 | 58.0 |
| 23 | p-HEMA (tetrahydrofurane and diethylether) | 77.8 | 54.0 |
| 24 | PVA (acetonitril) | 47.1 | 37.5 |

EXAMPLE 25 to 27

Examples 22 to 24 are repeated with the same 2,4-TDI solution modified films, but using, instead of the step of soaking in a chitosan solution, the step of soaking in a 1% solution of hyaluronic acid, comprising about 1 mg of catalyst (DBTDL), in DMSO.

The following table lists the contact angles ("CA"), measured with a system G 40 (Krüss GmbH, Hamburg Germany), of the polymeric films before treatment and after treatment:

| Example | Material | CA before treatment (°) | CA after treatment (°) |
|---|---|---|---|
| 25 | polybutadiene | 79.5 | 59.1 |
| 26 | p-HEMA | 78.0 | 55.1 |
| 27 | PVA | 48.0 | 38.0 |

EXAMPLE 28

Washed and lyophilized SID™ contact lenses (from CIBA Vision, Atlanta, Tefilcon), based on a crosslinked polymer of p-HEMA, are soaked in a mixture of 5 ml of tetrahydrofurane, 5 ml of diethylether, 0.2 g of isophorone diisocyanate (IPDI) and 10 mg of catalyst (DBTDL). The reaction proceeds at room temperature under nitrogen flow for 12 hours. Thereafter the lenses are washed with acetone, dried and soaked in a 0.5% solution of a carbohydrate in DMSO (comprising 5% LiCl) and (except for example 28 d) DBTDL as a catalyst. After 1 to 2 hours the lenses are vigorously washed with water, dried and analyzed.

The following table lists the contact angles ("CA"), measured with a system G 40 (Krüss GmbH, Hamburg Germany), of the contact lenses after treatment (for comparison: the contact angle of an untreated STD contact lens is 77–78°):

| Example | carbohydrate | CA after treatment (°) |
|---|---|---|
| a) | Mucin (Sigma) | 53.4 |
| b) | Fucoidan | 50.5 |
| c) | Dextran | 26.8 |
| d) | Glucosamine (Fluka) | 38.9 |

EXAMPLE 29

Washed and lyophilized EXCELENS™ contact lenses (from CIBA Vision, Atlanta, Adlafilcon), based on a crosslinked polymer of PVA, are soaked in a mixture of 5 ml of tetrahydrofurane, 5 ml of diethylether, 0.2 g of isophorone diisocyanate (IPDI) and 10 mg of catalyst (DBTDL). The reaction proceeds at room temperature under nitrogen for 12 hours. Thereafter the lenses are washed with acetone, dried and soaked in a 0.5% solution of a carbohydrate in DMSO (comprising 5% LiCl) and (except for example 29 a) DBTDL as a catalys. After 1 to 2 hours the lenses are vigorously washed with water, dried and analyzed.

The following table lists the contact angles ("CA"), measured with a system G 40 (Krüss GmbH, Hamburg Germany), of the contact lenses after treatment (for comparison: the contact angle of an untreated EXCELENS contact lens is 69–70°):

| Example | carbohydrate | CA after treatment (°) |
|---|---|---|
| a) | Chitosan | 63.1 |
| b) | Fucoidan (Sigma) | 61.3 |
| c) | Dextran (Fluka) | 44.9 |

EXAMPLE 30

A flat substrate of fluorinated ethylene propylene (FEP) or perfluoropolyether (PFPE) is subjected to a plasma treatment in the presence of a) ammonia, b) ethylene diamine or c) heptylamine. Dextran of 74.2 kDa molecular weight is treated with $NaIO_4/NaCNBH_3$ and reacted with the plasma treated substrate having amino groups at its surface. A substrate with a hydrophilic coating is obtained for which the following time taken for water to recede from 50% of the surface (WRT) is measured:

|  | substrate | plasma gas | WRT (sec) |
|---|---|---|---|
| a) | FEP | ammonia | 160 |
| b) | FEP | ethylene diamine | 160 |
| c) | PFPE | heptylamine | 110 |

EXAMPLE 31

Different contact lenses are subjected to a plasma treatment in the presence of ammonia or heptylamine. Dextran of 74.2 kDa molecular weight is treated with $NaIO_4/NaCNBH_3$ and reacted with the plasma treated contact lenses having amino groups at their surface. Contact lenses with a hydrophilic coating are obtained for which the following time taken for water to recede from 50% of the surface (WRT) is measured:

|  | contact lens material | plasma gas | WRT (sec) |
|---|---|---|---|
| a) | Tefilcon | ammonia | 60 |
| b) | silicone material* | ammonia | 115 |
| c) | silicone material* | heptylamine | 100 |
| d) | Atlafilcon A | heptylamine | 130 |

*The silicone material used here is a copolymer comprising 15 weight percent methyl methacrylate, 15 weight percent tris(trimethylsilyloxy)silylpropyl methacrylate and 70 weight percent of a macromer having units of hydroxybutyl-terminated dimethylsiloxane, and of isophorone diisocyanate the isocyanate groups of which have been reacted with the terminal hydroxy groups of the siloxane, which macromer is terminated with isocyanatoethyl methacrylate, the isocyanato groups of which have been reacted with a terminal hydroxy group of the siloxane.

What is claimed is:

1. A composite materials having at least one wettable surface capable of holding a continuous layer of aqueous fluid therein, which material comprises:
   (a) a bulk base material, and
   (b) a hydrophilic coating, wherein the hydrophilic coating consists of a carbohydrate directly and covalently attached to amino groups at the surface of the bulk base material, wherein said amino groups are either inherently (a priori) present in the base material or have been attached to the surface of the bulk base material by plasma surface treatment.

2. A composite material according to claim 1 wherein the amino groups are inherently present in the base material.

3. A composite material according to claim 1 which is a biomedical device.

4. A composite material according to claim 1 which is an ophthalmic device.

5. A composite material according to claim 1 which is a contact lens.

6. A composite material according to claim 1 wherein the carbohydrate is selected from dextran, chitosan, hyaluronic acid, mucin, fucoidan, and glucosamine.

7. A composite material according to claim 1 wherein said amino groups have been directly and covalently attached to said surface by plasma surface treatment.

8. A composite material according to claim 1 wherein said amino groups have been directly and covalently attached to said surface by plasma surface treatment and the carbohydrate is a polysaccharide.

9. A composite material according to claim 8 wherin the carbohydrate is selected from dextran, chitosan, hyaluronic acid, mucin, fucoidan, and glucosamine.

10. A composite material according to claim 1 wherein amino groups are inherently present in the base material wherein the carbohydrate is a polysaccharide.

11. A composite material according to claim 10 wherin the carbohydrate is selected from dextran, chitosan, hyaluronic acid, mucin, fucoidan, and glucosamine.

12. A composite material according to claim 1 wherein amino groups are inherently present in the base material, wherein the carbohydrate is a non-polysaccharide carbohydrate with is directly attached to the amino groups.

13. A composite material according to claim 1 wherein amino groups are inherently present in the base material, wherein the carbohydrate is dextran.

14. A process for the manufacture of a wettable composite material with one or more wettable surface capable of holding a continuous layer of aqueous fluid thereon, wherein said composite material includes a bulk base material and a hydrophilic coating of a carbohydrate directly attached covalently to amino groups at the surface of the base materials, said process comprising the steps of:

(1) covalently attaching amino groups onto the surface of a preformed base material by subjecting the preformed base material to a gas plasma established in a vapor containing at least one amine compound;

(2) optionally treating the carbohydrate with a reagent which modifies said carbohydrate such that said carbohydrate is capable of reacting with the amino groups;

(3) reacting said amino groups on the surface with the carbohydrate to immobilize the carbohydrate onto the surface; and (4) optionally treating the surface-immobilized carbohydrate with a reagent to stabilize the bond between the carbohydrate and the surface.

15. A composite material according to claim 1, wherein the amino groups are covalently attached to the surface of preformed base material by subjecting the preformed base material to a low pressure plasma in a vapor of an alkylamine having up to eight carbon atoms under conditions whereby amino groups are formed on the desired surface of the base material.

16. A composite material according to claim 15 wherein the alkyl amine is heptylamine.

17. A composite material according to claim 15 wherein the alkyl amine is ethylamine.

18. A composite material according to claim 15 wherein the alkyl amine is methylamine.

19. A process of claim 14 wherein the amine is an alkyl amine having up to eight carbon atoms.

20. A process of claim 14 wherein the alkyl amine is heptylamine.

21. A process of claim 14 wherein the alkyl amine is ethylamine.

22. A process of claim 14 wherein the alkyl amine is methylamine.

* * * * *